(12) United States Patent
Bystrom et al.

(10) Patent No.: US 6,599,258 B1
(45) Date of Patent: *Jul. 29, 2003

(54) RESUSCITATION DEVICE

(75) Inventors: Steven R. Bystrom, Portola Valley, CA (US); Darren R. Sherman, Portola Valley, CA (US); Kenneth H. Mollenauer, Portola Valley, CA (US)

(73) Assignee: Revivant Corporation, Sunnyvale, CA (US)

( * ) Notice: Subject to any disclaimer, the term of this patent is extended or adjusted under 35 U.S.C. 154(b) by 230 days.

This patent is subject to a terminal disclaimer.

(21) Appl. No.: 09/615,979

(22) Filed: Jul. 14, 2000

Related U.S. Application Data

(63) Continuation of application No. 08/924,555, filed on Aug. 27, 1997, now Pat. No. 6,090,056.

(51) Int. Cl.$^7$ .............................................. A61H 31/00
(52) U.S. Cl. ........................................ 601/41; 601/44
(58) Field of Search ................................ 601/1, 41–44, 601/134, 135; 434/265; 340/298, 573, 539, 568, 571, 531, 533; 379/38, 40, 41, 45, 42; 455/401; 607/3, 9, 6, 8

(56) References Cited

U.S. PATENT DOCUMENTS

| | | |
|---|---|---|
| 2,071,215 A | 2/1937 | Petersen |
| 2,699,163 A | 1/1955 | Engstrom |
| 2,754,817 A | 7/1956 | Nemeth |
| 2,780,222 A | 2/1957 | Polzin et al. |
| 2,853,998 A | 9/1958 | Emerson |
| 2,899,955 A | 8/1959 | Huxley, III et al. |
| 3,042,024 A | 7/1962 | Mendelson |
| 3,120,228 A | 2/1964 | Huxley, III |
| 3,368,550 A | 2/1968 | Glascock |
| 3,461,860 A | 8/1969 | Barkalow et al. |
| 3,481,327 A | 12/1969 | Drennen |
| 3,782,371 A | 1/1974 | Dorouineau |
| 4,397,306 A | 8/1983 | Weisfeldt et al. |
| 4,570,615 A | 2/1986 | Barkolow |
| 4,664,098 A | 5/1987 | Woudenberg et al. |
| 4,702,231 A | 10/1987 | Arpin |
| 4,829,285 A | 5/1989 | Brand et al. .................. 379/38 |
| 4,915,095 A | 4/1990 | Chun |
| 4,928,674 A | 5/1990 | Halperin et al. |
| 5,056,505 A | 10/1991 | Warwick et al. |
| 5,098,369 A | 3/1992 | Heilman et al. .............. 600/16 |
| 5,184,606 A | 2/1993 | Csorba |
| 5,217,010 A | 6/1993 | Tsitlik et al. |
| 5,222,478 A | 6/1993 | Scarberry et al. |
| 5,228,449 A | 7/1993 | Christ et al. ................ 600/503 |
| 5,257,619 A | 11/1993 | Everete |
| 5,277,194 A | 1/1994 | Hosterman et al. |
| 5,295,481 A | 3/1994 | Geeham ...................... 601/43 |
| 5,327,887 A | 7/1994 | Nowakowski |
| 5,359,999 A | 11/1994 | Kinsman ..................... 601/41 |
| 5,399,148 A | 3/1995 | Waide et al. ................. 601/41 |
| 5,405,362 A | 4/1995 | Kramer ......................... 607/5 |
| 5,416,826 A | 5/1995 | Butler ......................... 379/40 |
| 5,474,533 A | 12/1995 | Ward et al. ................... 604/26 |
| 5,490,820 A | 2/1996 | Schock et al. ................ 601/41 |
| 5,554,975 A | 9/1996 | Hall et al. ................... 340/573 |

(List continued on next page.)

Primary Examiner—Danton D. DeMille
(74) Attorney, Agent, or Firm—K. David Crockett, Esq.; Crockett & Crockett

(57) ABSTRACT

A resuscitation device for automatic compression of victim's chest using a compression belt which exerts force evenly over the entire thoracic cavity. The belt is constricted and relaxed through a motorized spool assembly which repeatedly tightens the belt and relaxes the belt to provide repeated and rapid chest compression. An assembly includes various resuscitation devices including chest compression devices, defibrillation devices, and airway management devices, along with communications devices and senses with initiate communications with emergency medical personnel automatically upon use of the device.

3 Claims, 14 Drawing Sheets

U.S. PATENT DOCUMENTS

| | | | |
|---|---|---|---|
| 5,593,426 A | * 1/1997 | Morgan et al. | 128/903 |
| 5,630,789 A | 5/1997 | Schock et al. | 601/41 |
| 5,644,294 A | 7/1997 | Ness | 340/573 |
| 5,664,563 A | 9/1997 | Schroeder et al. | |
| 5,673,304 A | 9/1997 | Connor et al. | 379/38 |
| 5,694,452 A | 12/1997 | Bertolet | 379/38 |
| 5,738,637 A | 4/1998 | Kelly et al. | 601/41 |
| 5,792,190 A | * 8/1998 | Olson et al. | 607/5 |
| 5,866,711 A | * 2/1999 | Hung et al. | 560/167 |

* cited by examiner

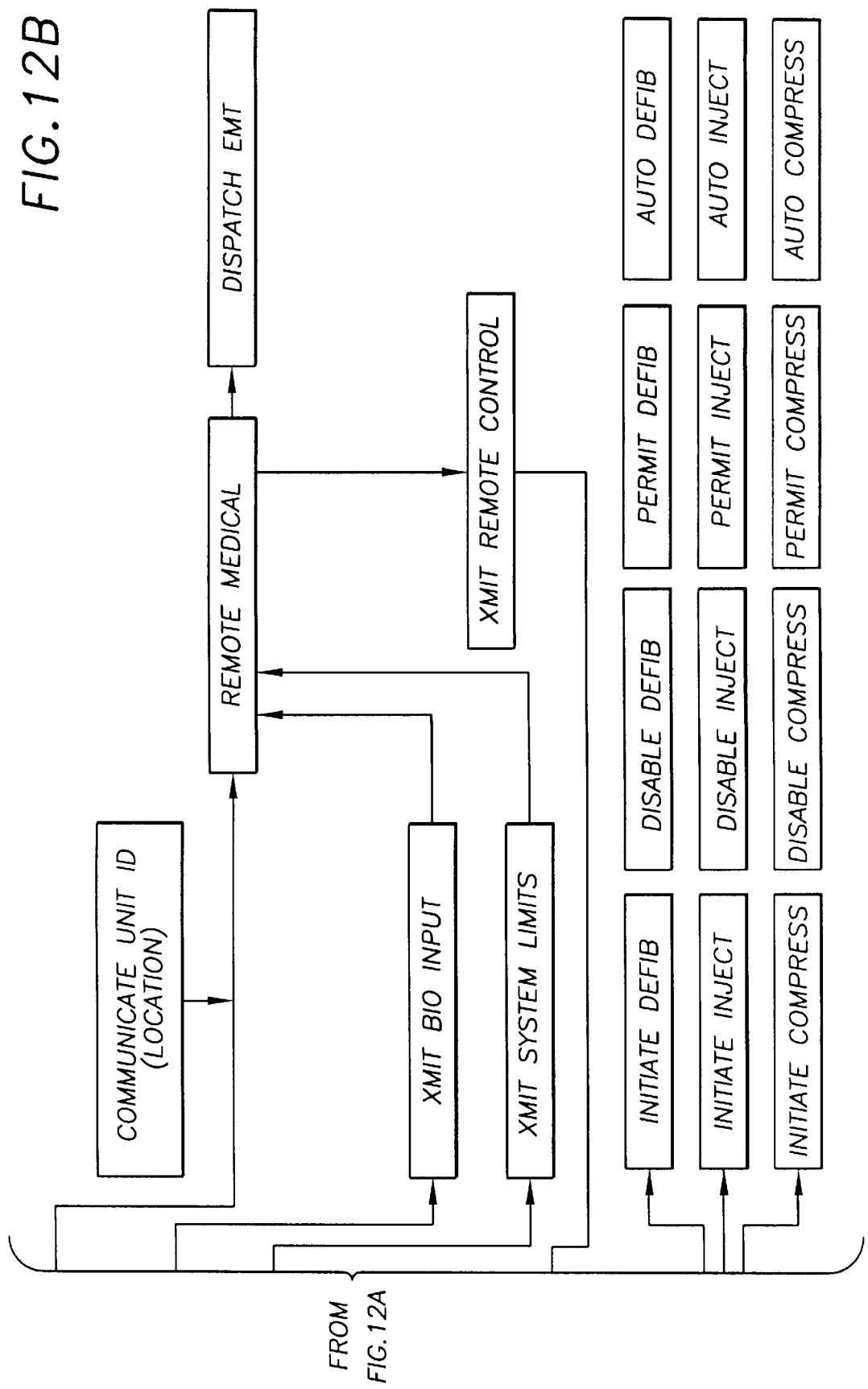

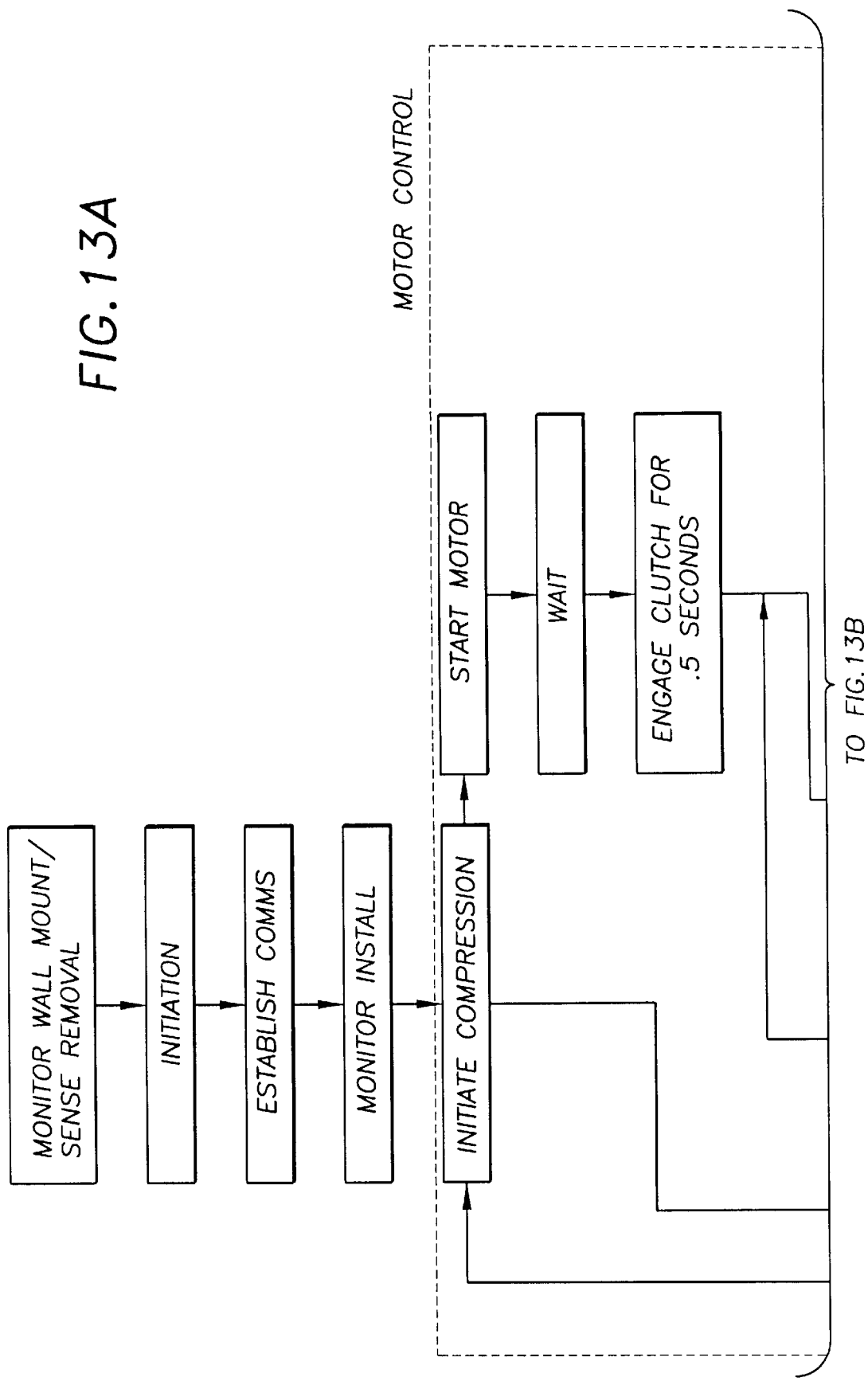

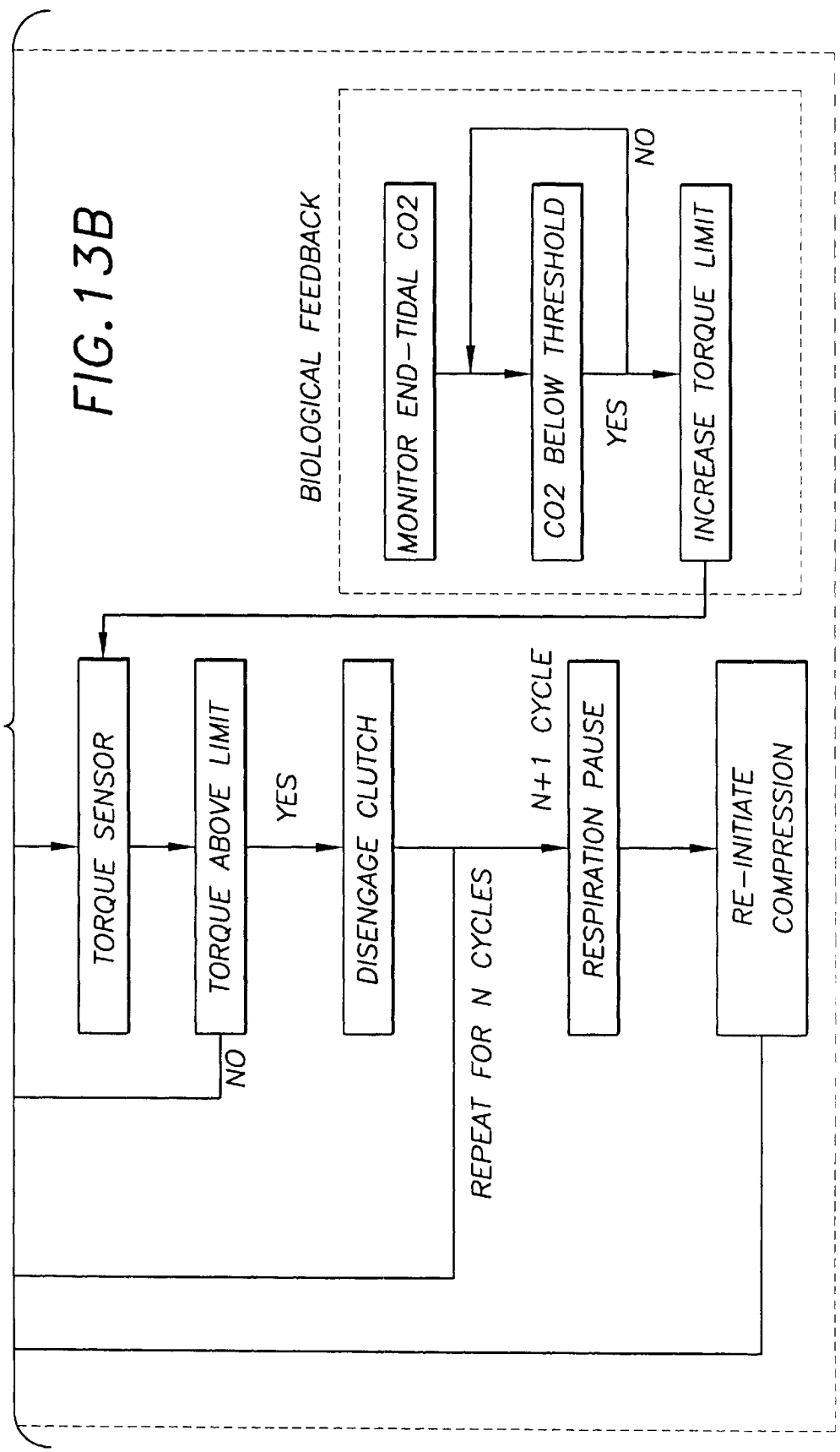

RESUSCITATION DEVICE

RELATED PATENT APPLICATIONS

This application is a continuation of application 08/924,555, filed Aug. 27, 1997 now U.S. Pat. No. 6,090,056.

FIELD OF THE INVENTION

This invention relates to emergency medical devices and methods.

BACKGROUND OF THE INVENTION

Cardiopulmonary resuscitation (CPR) is a well-known and valuable method of first aid. CPR is used to resuscitate people who have suffered from cardiac arrest after heart attack, electric shock, chest injury and many other causes. During cardiac arrest, the heart stops pumping blood, and a person suffering cardiac arrest will soon suffer brain damage from lack of blood supply to the brain. Thus, CPR requires repetitive chest compression to squeeze the heart and the thoracic cavity to pump blood through the body. Very often, the victim is not breathing, and mouth to mouth artificial respiration or a bag valve mask is used to supply air to the lungs while the chest compression pumps blood through the body.

It has been widely noted that CPR and chest compression can save cardiac arrest victims, especially when applied immediately after cardiac arrest. Chest compression requires that the person providing chest compression repetitively push down on the sternum of the victim at 80–100 compressions per minute. CPR and closed chest compression can be used anywhere, wherever the cardiac arrest victim is stricken. In the field, away from the hospital, it may be accomplished by ill-trained by-standers or highly trained paramedics and ambulance personnel.

When a first aid provider performs chest compression well, blood flow in the body is typically about 25–30% of normal blood flow. This is enough blood flow to prevent brain damage. However, when chest compression is required for long periods of time, it is difficult if not impossible to maintain adequate compression of the heart and rib cage. Even experienced paramedics cannot maintain adequate chest compression for more than a few minutes. Hightower, et al., Decay In Quality Of Chest Compressions Over Time, 26 Ann. Emerg. Med. 300 (September 1995). Thus, long periods of CPR, when required, are not often successful at sustaining or reviving the victim. At the same time, it appears that, if chest compression could be adequately maintained, cardiac arrest victims could be sustained for extended periods of time. Occasional reports of extended CPR efforts (45–90 minutes) have been reported, with the victims eventually being saved by coronary bypass surgery. See Tovar, et al., Successful Myocardial Revascularization and Neurologic Recovery, 22 Texas Heart J. 271 (1995).

In efforts to provide better blood flow and increase the effectiveness of bystander resuscitation efforts, modifications of the basic CPR procedure have been proposed and used. Of primary concern in relation to the devices and methods set forth below are the various mechanical devices proposed for use in main operative activity of CPR, namely repetitive compression of the thoracic cavity.

The device shown in Barkolow, Cardiopulmonary resuscitator Massager Pad, U.S. Pat. No. 4,570,615 (Feb. 18, 1986), the commercially available Thumper device, and other such devices, provide continuous automatic closed chest compression. Barkolow and others provide a piston that is placed over the chest cavity and supported by an arrangement of beams. The piston is placed over the sternum of a patient and set to repeatedly push downward on the chest under pneumatic power. The victim must first be installed into the device, and the height and stroke length of the piston must be adjusted for the patient before use, leading to delay in chest compression. Other analogous devices provide for hand operated piston action on the sternum. Everette, External Cardiac Compression Device, U.S. Pat. No. 5,257,619 (Nov. 2, 1993), for example, provides a simple chest pad mounted on a pivoting arm supported over a patient, which can be used to compress the chest by pushing down on the pivoting arm. These devices are not clinically more successful than manual chest compression. See Taylor, et al., External Cardiac Compression, A Randomized Comparison of Mechanical and Manual Techniques, 240 JAMA 644 (August 1978). Other devices for mechanical compression of the chest provide a compressing piston that is secured in place over the sternum via vests or straps around the chest. Woudenberg, Cardiopulmonary Resuscitator, U.S. Pat. No. 4,664,098 (May 12, 1987) shows such a device which is powered with an air cylinder. Waide, et al., External Cardiac Massage Device, U.S. Pat. No. 5,399,148 (Mar. 21, 1995) shows another such device which is manually operated. In another variation of such devices, a vest or belt designed for placement around the chest is provided with pneumatic bladders that are filled to exert compressive forces on the chest. Scarberry, Apparatus for Application of Pressure to a Human Body, U.S. Pat. No. 5,222,478 (Jun. 29, 1993) and Halperin, Cardiopulmonary Resuscitation and Assisted Circulation System, U.S. Pat. No. 4,928,674 (May 29, 1990) show examples of such devices.

Several operating parameters must be met in a successful resuscitation device. Chest compression must be accomplished vigorously if it is to be effective. Very little of the effort exerted in chest compression actually compresses the heart and large arteries of the thorax and most of the effort goes into deforming the chest and rib cage. The force needed to provide effective chest compression creates risk of other injuries. It is well known that placement of the hands over the sternum is required to avoid puncture of the heart during CPR. Numerous other injuries have been caused by chest compression. See Jones and Fletter, Complications After Cardiopulmonary Resuscitation, 12 AM. J. Emerg. Med. 687 (November 1994), which indicates that lacerations of the heart, coronary arteries, aortic aneurysm and rupture, fractured ribs, lung herniation, stomach and liver lacerations have been caused by CPR. Thus the risk of injury attendant to chest compression is high, and clearly may reduce the chances of survival of the victim vis-à-vis a resuscitation technique that could avoid those injuries. Chest compression will be completely ineffective for very large or obese cardiac arrest victims because the chest cannot be compressed enough to cause blood flow. Chest compression via pneumatic devices is hampered in its application to females due to the lack of provision for protecting the breasts from injury and applying compressive force to deformation of the thoracic cavity rather than the breasts.

CPR and chest compression should be initiated as quickly as possible after cardiac arrest to maximize its effectiveness and avoid neurologic damage due to lack of blood flow to the brain. Hypoxia sets in about two minutes after cardiac arrest, and brain damage is likely after about four minutes without blood flow to the brain, and the severity of neurologic defect increases rapidly with time. A delay of two or three minutes significantly lowers the chance of survival and increases the probability and severity of brain damage. However, CPR and ACLS are unlikely to be provided within this time frame. Response to cardiac arrest is generally considered to occur in four phases, including action by Bystander CPR, Basic Life Support, Advanced Life Support, and the Emergency Room. By-stander CPR occurs, if at all, within the first few minutes after cardiac arrest. Basic Life Support is provided by First Responders who arrive on scene about 4–6 minutes after being dispatched to the scene. First responders include ambulance personnel, emergency medical technicians, firemen and police. They are generally capable of providing CPR but cannot provide drugs or intravascular access, defibrillation or intubation. Advanced Life Support is provided by paramedics or nurse practitioners who generally follow the first responders and arrive about 8–15 minutes after dispatch. ACLS is provided by paramedics, nurse practitioners or emergency medical doctors who are generally capable of providing CPR, drug therapy including intravenous drug delivery, defibrillation and intubation. The ACLS providers may work with a victim for twenty to thirty minutes on scene before transporting the victim to a nearby hospital. Though defibrillation and drug therapy is often successful in reviving and sustaining the victim, CPR is often ineffective even when performed by well-trained first responders and ACLS personnel because chest compression becomes ineffective when the providers become fatigued. Thus, the initiation of CPR before arrival of first responders is critical to successful life support. Moreover, the assistance of a mechanical chest compression device during the Basic Life Support and Advanced Life Support stages is needed to maintain the effectiveness of CPR.

SUMMARY

The devices described below provide for circumferential chest compression with a device which is compact, portable or transportable, self-powered with a small power source, and easy to use by by-standers with little or no training. Additional features may also be provided in the device to take advantage of the power source and the structural support board contemplated for a commercial embodiment of the device.

In its simplest form, the device includes a broad belt which wraps around the chest and is buckled in the front of the cardiac arrest victim. The belt is repeatedly tightened around the chest to cause the chest compression necessary for CPR. The buckles and/or front portion of the belt are anatomically accommodating for the female breast, or for the obese person, so that the device is effective for women as well as men. The buckle may include an interlock which must be activated by proper attachment before the device will activate, thus preventing futile belt cycles. The operating mechanism for repeatedly tightening the belt is provided in a support board, and comprises a rolling mechanism which takes up the intermediate length of the belt to cause constriction around the chest. The roller is powered by a small electric motor, and the motor powered by batteries and/or standard electrical power supplies such as 120V household electrical sockets or 12V DC automobile power sockets (car cigarette lighter sockets). (An initial prototype used a power drill with a single 9.6V rechargeable battery, and provided powerful chest compression for about ten minutes.) The batteries and any necessary transformers may be housed in the support board, and the support board may be made in sizes useful for supporting the victim's head, adequate for storing batteries and other accessories, and convenient for mounting within office buildings, factories, airplanes and other areas of potential need. Thus, numerous inventions are incorporated into the portable resuscitation device described below.

The portable resuscitation device may incorporate a number of features and accessories that aid in the administration of CPR and other therapy. By-standers may be unable to confidently determine if chest compression is needed, or when it should be stopped. Accordingly, the device may be combined with an interlock system including a heart monitor or EKG which diagnoses the condition of the patient, and circuitry or a computer which initiates, permits or forbids belt operation accordingly. The power supply provided for belt constriction may also be used to provide power for defibrillation (an appropriate treatment for many cardiac arrests). Again, bystanders will most likely not be capable of determining when defibrillation is appropriate, and the defibrillation portion of the device may be provided with an interlock system including the heart monitor or EKG which diagnoses the condition of the patient and circuitry which initiates, permits, or forbids defibrillation. Expert systems implemented through the circuitry or computer modules can accomplish these functions.

Automatic, computer driven therapy of this nature may provide early and appropriate life saving response to many cardiac arrest patients whom would otherwise die. However, some situations in which the device might be used may call for expert supervision of the CPR process by emergency medical technicians, emergency room doctors, or cardiologists. To this end, the expert systems mentioned above may be replaced with the expert diagnosis and decision-making of medical personnel through a telemetry system housed within the support board of the device. The support board can include a telemetry system which automatically dials medical personnel in a nearby hospital, emergency medical crew, ambulance, or even a central diagnostic and control facility. Interlocks, limit switches and other typical sensors can be used to sense the proper position and closure of the belt about the chest of the patient. Heart monitors and EKG electrodes can sense the heart rate and EKG of the victim. Using communication equipment within the device, this information can be communicated from the device to medical personnel remote from the victim. Through the same system, the medical personnel can communicate the device to initiate, permit or prohibit belt constriction or defibrillation, as dictated by preferred medical procedures. Communication can be established through normal telephone lines and a cordless telephone, or through a cellular telephone system, paging system, internet or any other communications system. The device can be programmed with location information, or provided with GPS capabilities to determine the location of the device, and this information can be automatically transmitted to an emergency response system such as the 911 system when the system is placed in use.

BRIEF DESCRIPTION OF THE DRAWINGS

FIG. 13 is a block diagram of the motor control system.

DETAILED DESCRIPTION OF THE INVENTION

Figure 1:
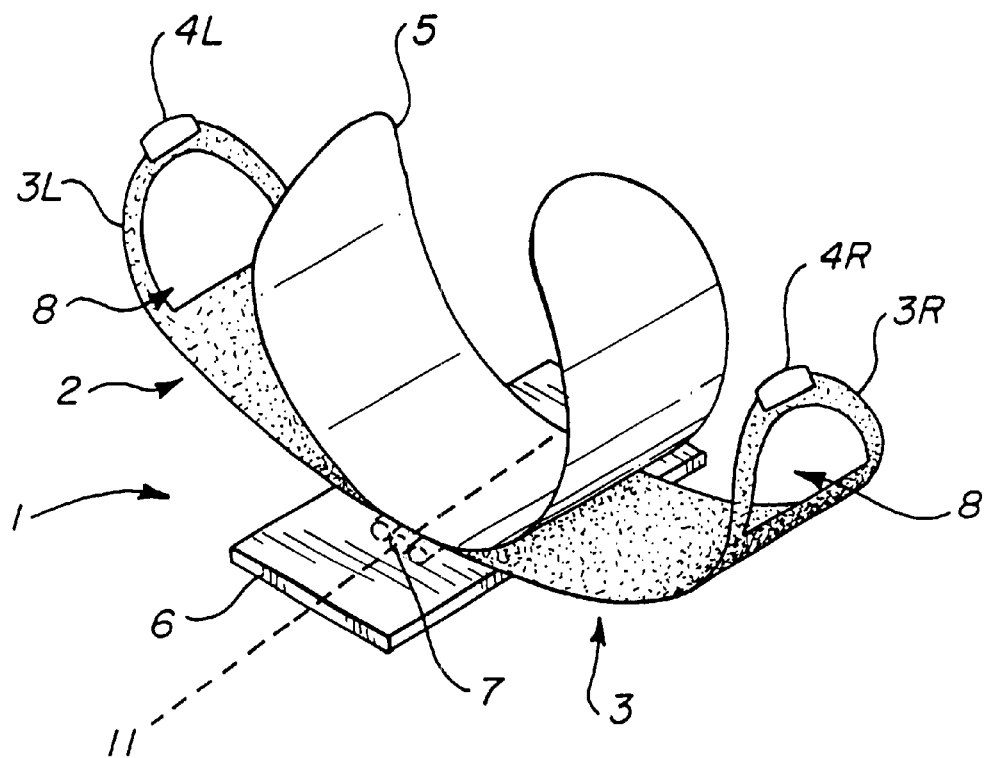
FIG. 1 is an overview of the resuscitation device, showing the inner and outer vests partially open.

FIG. 1 shows a simplified version of the resuscitation device 1. The mechanisms used for compressing the chest includes compression assembly 2 which includes a chest compression belt 3 with buckles 4L and 4R, a friction liner 5, a support board 6 and a motor driven spool assembly 7. The support board 6 is placed under a cardiac arrest victim, and the compression belt 3 and friction liner 5 are wrapped around the victim's chest. The chest compression belt, having a left side 3L and a right side 3R, is buckled over the victims chest by latching the buckles 4L and 4R together. In this configuration, the friction liner 5 will fit between the chest compression belt 3 and the victim and any clothes worn by the victim. The compression belt may be made of any strong material, and sailcloth has proven adequate for use. The compression belt may also be referred to as a vest, corset, girdle, strap or band. The friction liner may be made of Teflon®, tyvek™ or any other low friction material (by low friction, we mean a material that will permit sliding of the compression belt with less friction than expected between the belt and the victims clothing or bare skin). The friction liner may be made with any suitable lining material, as its purpose is to protect the victim from rubbing injury caused by the compression belt, and it may also serve to limit frictional forces impeding the compression belt operation. The friction liner can be provided in the form of a belt, vest, corset, girdle, strap or band, and may partially or completely encircle the chest.

Figure 2:
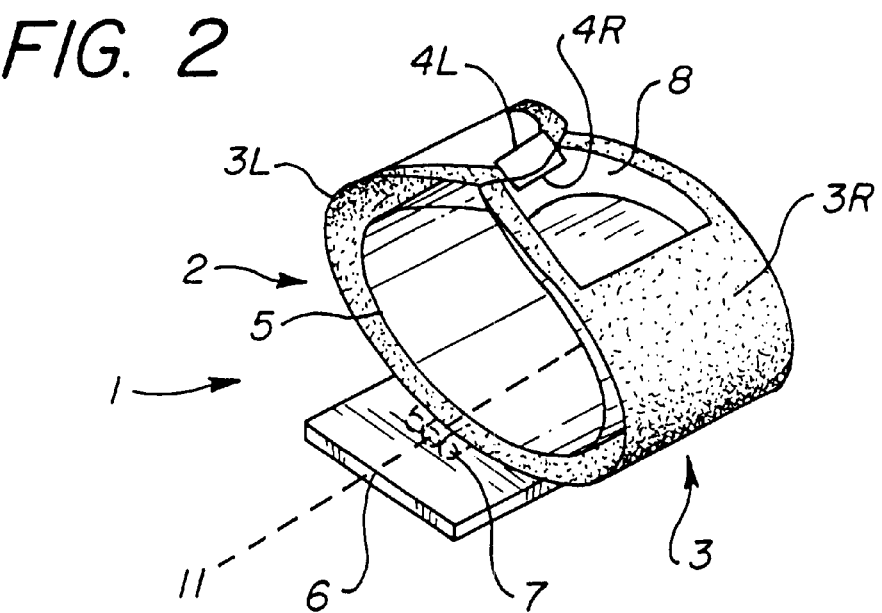
FIG. 2 is an overview of the resuscitation device in the buckled configuration.
Figure 3:
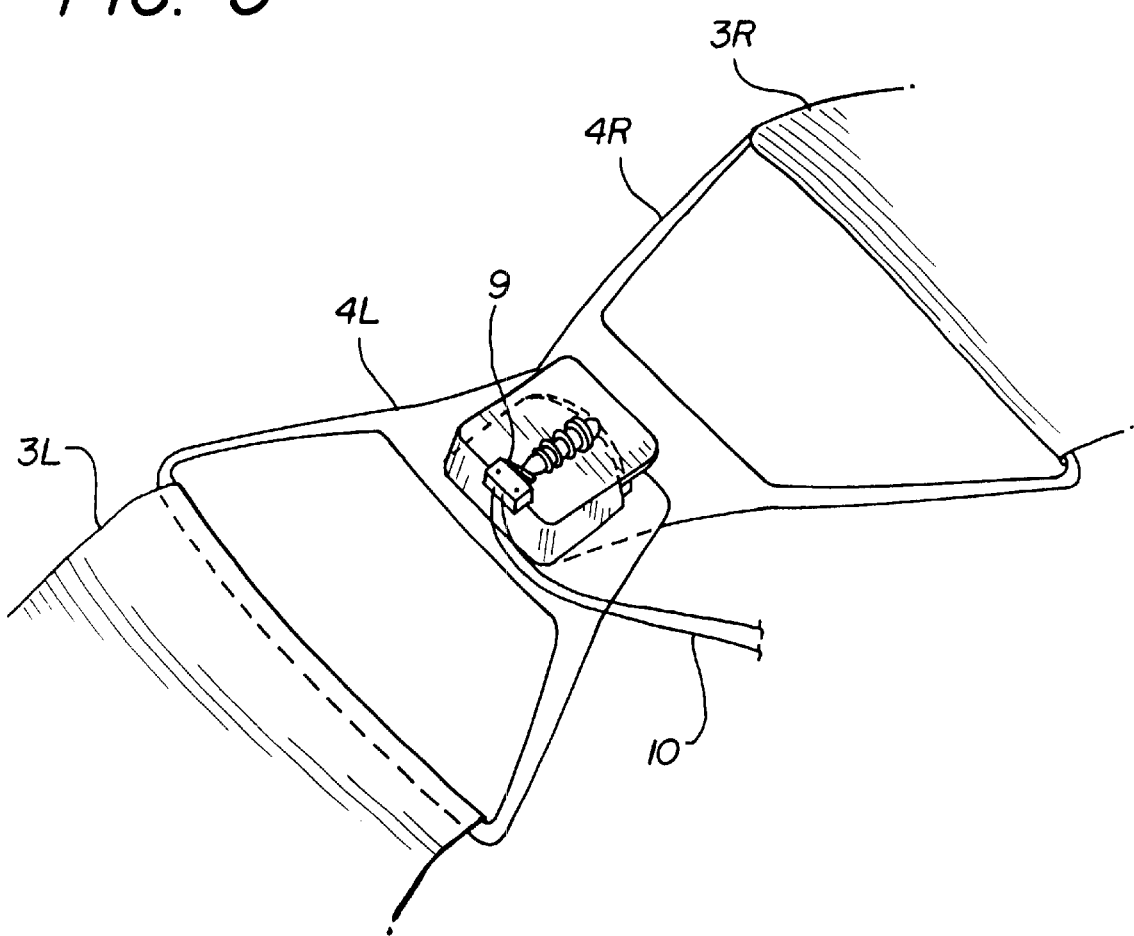
FIG. 3 is an detail view of the buckle used to close the device about a victim.

The front of the compression belt 3, including the buckles 4L and 4R, are configured to provide a broad pressure point over the sternum of the victim. This is illustrated in FIG. 2. Large openings 8 may be provided to accommodate female breasts and obese male breasts. The underside of the buckles 4L and 4R are smooth and broad, to distribute compressive force evenly over a wide area of the chest corresponding to the sternum. The point at which the buckle attaches to the chest compression belt may vary considerably, from the front of the chest to the back of the compression assembly, and the openings 8 may be provided in the buckles rather than the belt itself. FIG. 3 shows a detail of the buckles 4L and 4R used to fasten the compression belt about the chest of the victim. The buckle may be of any type, and preferably includes a latch sensing switch 9 operably connected through wire 10 to the motor control system (see FIG. 13) to indicate that the device has been buckled about the victims chest and is ready for the initiation of compression cycles. The buckles shown in FIG. 3 are D-ring shaped buckles with large openings 8, attached to the compression belt 3. Other fasteners and fastening means may be used.

Figure 4:
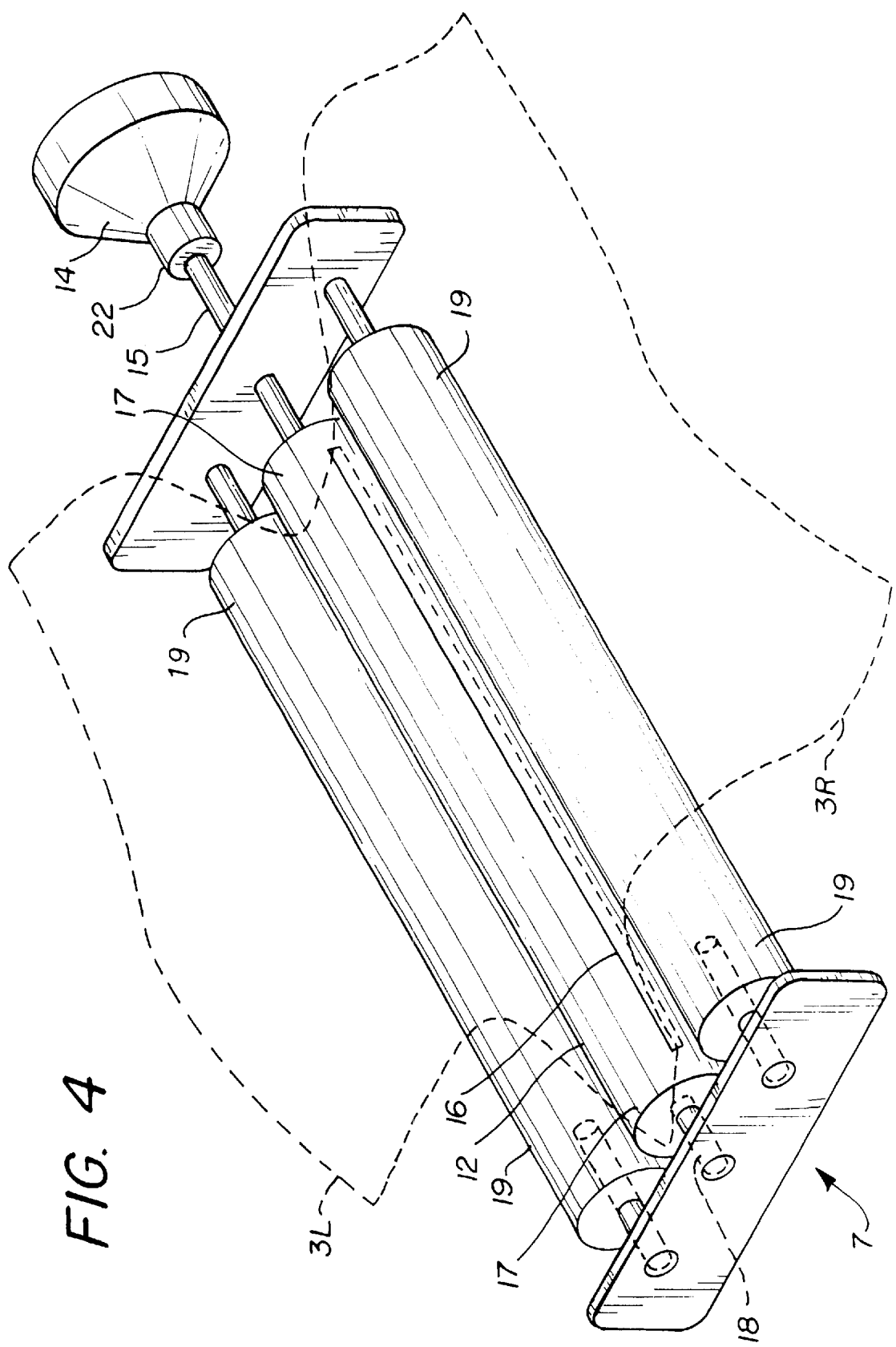
FIG. 4 shows the spool assembly used to operate the compression belt.

The chest compression belt 3 is repeatedly tightened about the chest of a victim through the action of one or more tightening spools which make up the spool assembly 7 located within the support board 6. The spool assembly, illustrated in FIG. 4, includes at least one spool or reel connected to the compression belt 3 at the back of the belt, preferably near the center or saggital line 11 of the compression belt (although it may be located on the front or side of compression belt). FIG. 4 shows a view of the spool assembly and its attachment to the compression belt. A spool assembly includes a single drive spool 12 operably connected to the motor 14 through drive shaft 15. The compression belt is secured to the drive spool in any suitable manner. In this case a longitudinal slot 16 provided in the drive spool 12. The slot extends radially or chordally through the drive spool, and extends axially for a length corresponding to the width of the compression belt, leaving the ends 17 solid for connection to the drive shaft 15 and journal shaft 18. The belt is slipped through the slot to created a secure connection between the belt and the drive spool. When secured in this manner, the rotation of the drive spool 12 will take up the right side of the compression belt 3R and the left side of the compression belt 3L and roll them up onto the spool, thus tightening the compression belt about the chest of the victim wearing the device. Spindles or alignment rollers 19 provide for alignment and low friction feed of the belt onto the roll created by operation of the drive shaft.

Figure 5:
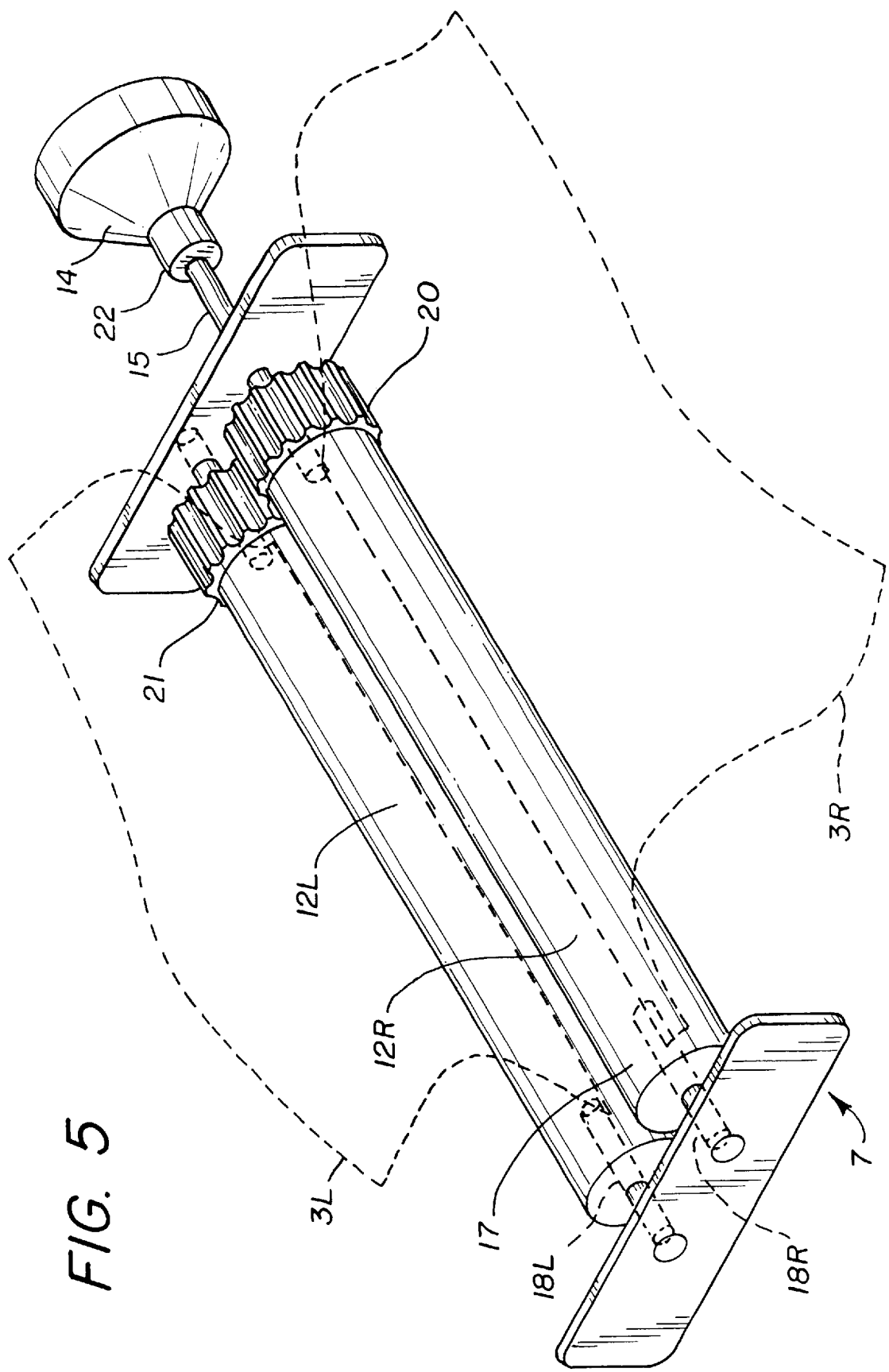
FIG. 5 shows an alternative embodiment of the spool assembly used to operate the compression belt.

Many alternative embodiments can be envisioned for the rolling mechanism, and one such alternative is illustrated in FIG. 5. Spools 12L and 12R are aligned in parallel and interconnected by a transmission gear 20 and planetary gear 21 and journaled upon shafts 18L and 18R. The drive shaft 15 is attached to spool 12R (or spool 12L) and operably attached to motor 14. The motor turns the shaft 15 and spool 12R in a counterclockwise direction to pull the right side of the compression belt 3R to the left and roll onto the spool. The transmission gear 20 acts upon the planetary gear 21 to cause clockwise rotation of spool 12L, which in turn pulls and wraps the left side of the compression belt 3L onto the spool 12L.

Thus, many embodiments of mechanisms which can cause repeated cyclic tightening of the compression vest about the chest of the victim may be envisioned. The compression belt serves to radially compress the chest through the cooperative action of the belt, board, and buckle, and to disperse the compressive force around the chest.

The motor is energized to rotate the spools and cause the compression belt to constrict around the chest of a victim. A motor such as a battery operated hand drill motor provides adequate chest compression for the purposes of CPR. To cause repetitive constriction of the compression belt 3, the motor 14 must be attached via a clutch 22 or other such mechanism. The motor 14 may be attached to the drive shaft 15 through a torque slipping clutching mechanism which engages the drive shaft until a high torque is achieved (indicating great resistance to further constriction, and thus indicating that the victim's chest has been compressed), and releases automatically upon such high torque, only to re-engage after the belt has been expanded in response to the normal elastic expansion of the victim's chest. In this manner, repetitive compression is achieved without need to repeatedly energize and de-energize the motor, thereby extending the length of operating time for any given battery supply. Alternatively, the motor may be repeatedly energized and de-energized, with the spools spinning freely during periods in which the belt is de-energized, wherein the clutch mechanism 22 will be similar to clutch mechanisms used on electric drills (which engage during operation of the drill but spin freely when the drill is de-energized). While the natural elastic expansion of the chest should make it unnecessary to drive the belt toward a loose condition, positive loosening may be achieved by reversing the motor or reversing the action of the motor through appropriate clutch or gear mechanisms. Timing of compressions is regulated through a computer module or a simple relay (windshield wiper style relays), and preferably will conform to standard of the Advanced Cardiac Life Support guidelines or Cardiopulmonary Resuscitation guidelines, or any other medically acceptable resuscitation regime. Current guidelines put forth by the American Heart Association call for 60–100 chest compressions per minute.

The motor is preferably battery powered, with provisions for taking power from any available power source. Batteries 23 may be stored within the support board 6. Three-volt batteries of convenient size, already available for use with numerous power tools, provide about five minutes of compression per battery, while twelve-volt batteries (1700 mA-h per battery) have provided about ten minutes of compression per battery. A thirty minute total battery capacity is desirable (corresponding to the estimated average time between cardiac arrest and transport to the hospital). Accordingly, several batteries may be installed within the support board and electrically connected to the motor and its controller. The batteries are provided with a trickle charge through a charger socket and charger plugged into 120V AC power when the device is not in use. (It is intended that the device be installed in factories, office buildings, airplanes and other facilities with relatively stable sources of power, and that the unit remain plugged in and charging when not in use.) If AC power is readily available at the site of use, the device may continue to run on AC power to preserve the batteries for later use. The unit may also be plugged into an automobile power jack with an appropriate auto adapter, thus providing for use where an automobile is the only source of power and for extended use in an ambulance.

Figure 6:
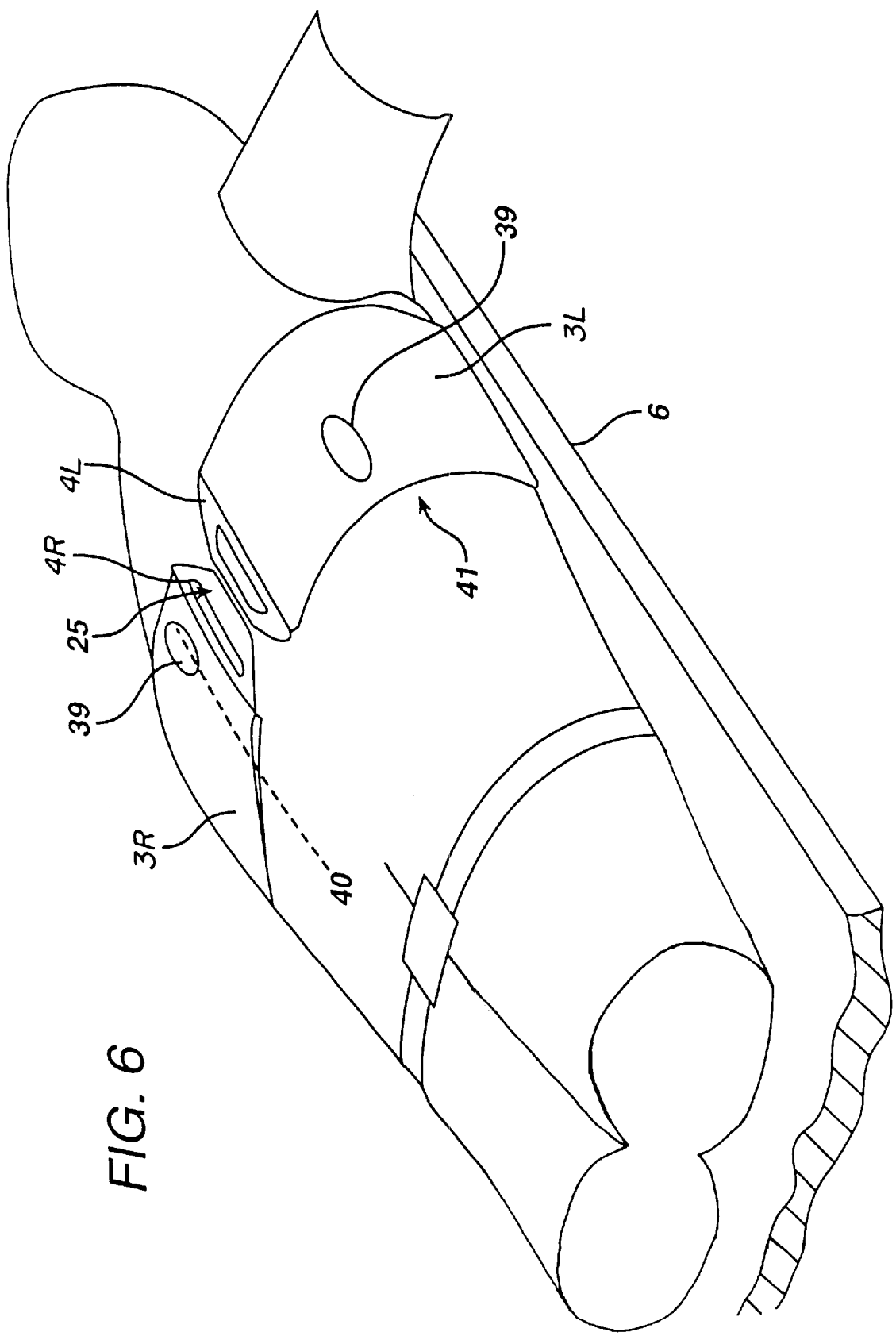
FIG. 6 is a view of the resuscitation device properly positioned on a victim.

FIG. 6 shows the resuscitation device installed on a cardiac arrest victim. The support board is placed under the victim, and the right and left portions of the compression belt are wrapped around the victim's chest and buckled over the front of the chest, indicated by arrow 25. Once in place, the system may be put into operation by manually starting the motors or by automatic initiation given the proper feedback from sensors located on the device, including the buckle latch sensors.

Figure 7:
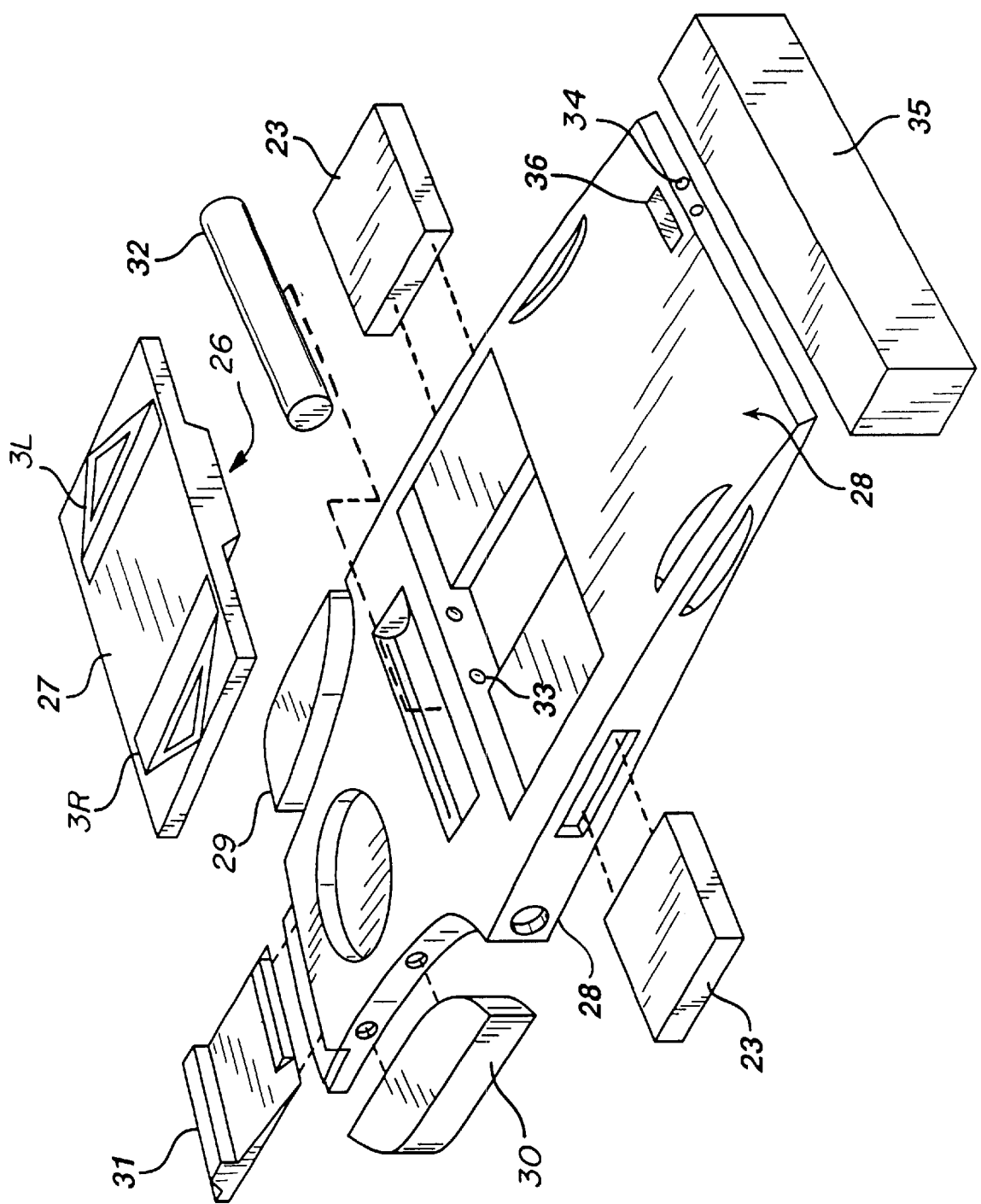
FIG. 7 shows the resuscitation device fitted with a number of additional devices for use during resuscitation.

A number of features may be combined with the basic system described above. The structure necessary for housing the operating mechanism for the belt, referred to as the support board above, can serve also as storage for additional devices used during resuscitation. FIG. 7 illustrates the resuscitation device 1 in a potential commercial embodiment. The support board 6 is sized to reach approximately from the lower lumbar region to the shoulders of a victim. The compression module 26 is separable from the support board 6, and includes the compression belt and friction vest stored within the compression module. The spool assembly and motor are also stored within the compression module, although the motor may also be installed in the support board. In this figure, the compression module comprises a small support board 27 which fits into the larger system support board 28. Taking advantage of available space in the system support board, a compartment 29 for storage of airway management devices (bag masks, oxygen masks, etc.), and a compartment 30 for storage of defibrillation equipment (electrodes and paddles, etc.) are included with the support board. A control and communication module 31 may also be incorporated into the support board. A small oxygen bottle 32 may be included, along with hoses routed to an accessible point on the board, and any connector desired for connection between the oxygen bottle and devices provided in the airway management compartment. Batteries 23 are stored within the support board (the number of the batteries chosen according the desired operating time, and the placement of the batteries dictated by available space). Batteries are operably connected to the motor in the compression module through electrical connectors 33 and appropriate wiring throughout the support board. The batteries can also be operably connected to the defibrillation module and control and communications module. Although long life batteries can be used, rechargeable batteries may be preferred. Accordingly, charging connection 34 on the support board is provided for charging the batteries or operating the device through outside power supplies.

The device is intended to be stored for long periods of time between uses, and storage holder 35 is provided for this purpose. The storage holder can include such necessities as power supply connectors, power plug, and a charging transformer. A removal sensor 36 is included in the support board to sense when the support board is removed from the storage holder (which, as described below, can be used as a condition indicating use of the device, and therefore the need to alert emergency medical personnel). The removal sensor can comprise a simple limit switch which senses physical removal of the system, and the limit switch can be used as a power switch or awaken switch which starts initiation of the system. The removal sensor can comprise a current sensor on the charging lines which treat cessation of charging current, increase in current draw through the charging system, or motor current as an indication of use. The choice of sensor may be made with many practical considerations in mind, such as the desire to avoid treating power outages as indications of use and other such unintended initiations. The state in which the device is deemed to be "in use" can be chosen according to the practical considerations, and in most instances it is expected that mere removal of the resuscitation device from the holder will constitute a clear signal someone has determined that a victim requires its use, and that emergency medical personnel should be dispatched to the location of the device. There are some environments in which later conditions will be used to indicate that the device is "in use," such as when installed in ambulances, airplanes, hospitals or other environments where it might be advisable to remove the device from its storage holder as a precaution or preparatory measure, and delay initiation of communications until the device is deployed or installed on the victim. In such cases, the buckle latch shown in FIG. 3 can be used as the sensor that indicates that the resuscitation device is in use.

Figure 8:
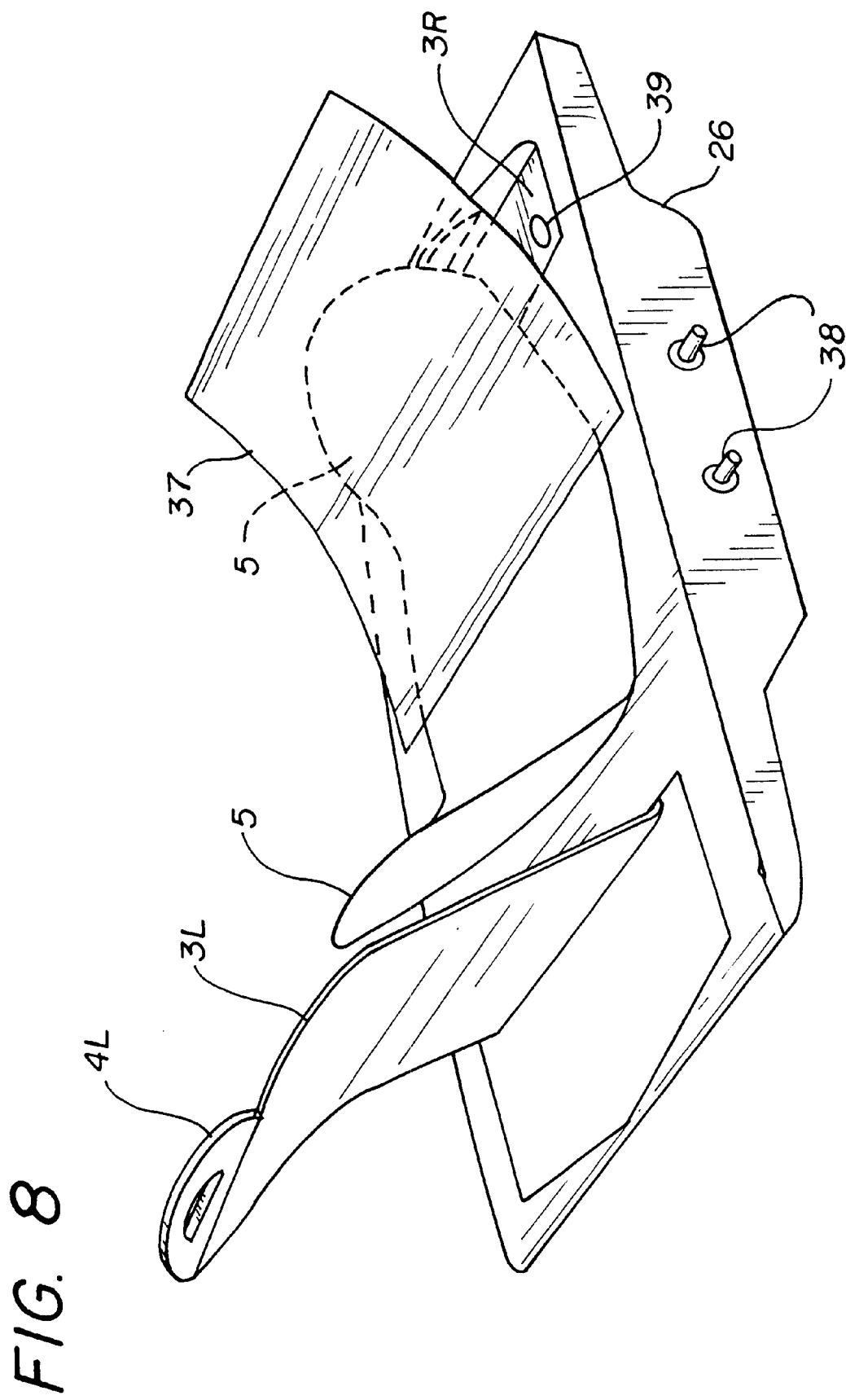
FIG. 8 shows a detail view of the CRP module of FIG. 7.

FIG. 8 shows the details of the compression module 26. When not in use, the module is covered with a tear sheet 37 that protects the compression belt from wear. The buckles are readily visible under the tear sheet. The electrical connectors 38 connect the batteries in the support board with the motor inside the compression module. The inside of the compression belt is fitted with penetrating electrodes 39 in the right sternum parasaggital location 40 and left rib medial location 41 for establishing the electrode contact needed for EKG sensing. These electrodes may be dispensed in environments where proper placement of the defibrillation electrodes can be assumed due to a high level of training amongst likely bystanders and first responders. The friction vest 5 is secured to the compression module above the spool assembly location.

Figure 9:
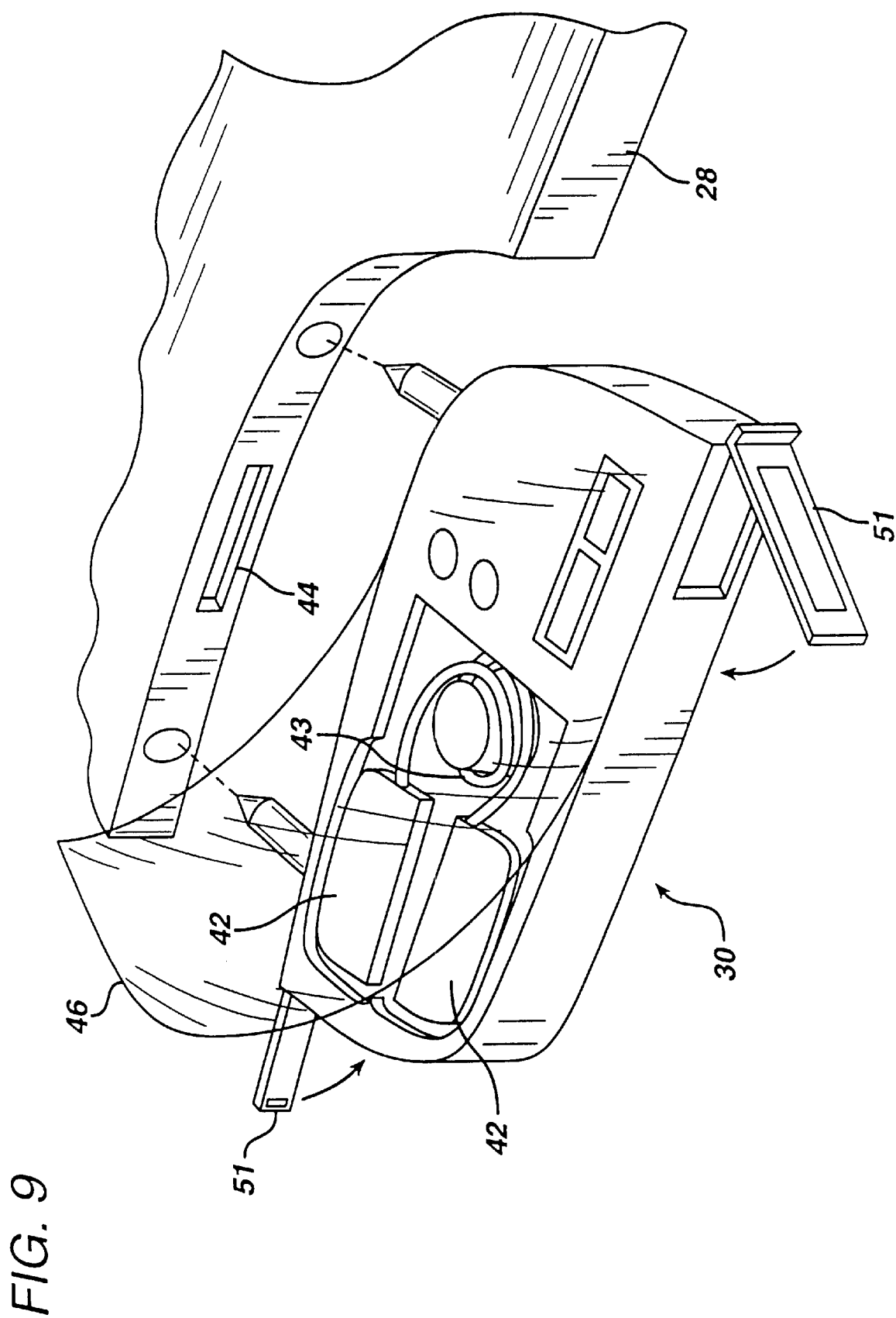
FIG. 9 shows a detail view of the defibrillation module of FIG. 7.
Figure 10:
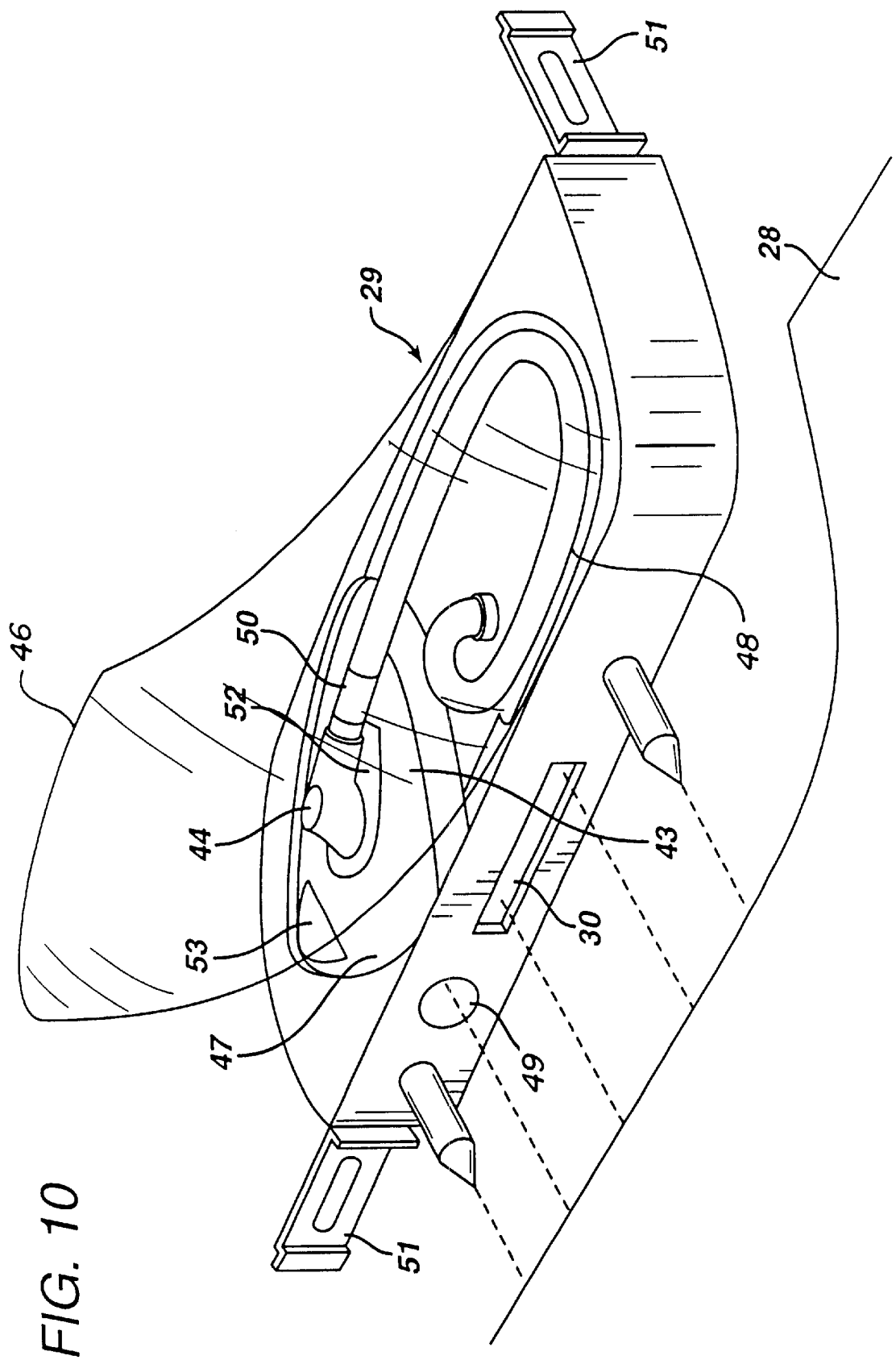
FIG. 10 shows a detail view of the airway management module of FIG. 7.

FIG. 9 shows a detail view of the defibrillation module in the compartment 30. The defibrillation module includes a pair of defibrillation electrodes 42 connected to the batteries through the power connections 43. The defibrillation electrodes will be controlled by circuitry housed within the defibrillation module, and may be connected to the control module through the data port 44. The defibrillation module is releasably attached to the support board 28 with quick release latches 51. Tear sheet 46 protects the components of the defibrillation module during storage and provides ready access for use. FIG. 10 shows the detail view of the airway management module in the compartment 29, which includes an oxygen mask 47, a length of tubing 48 and an air fitting 49 connecting the oxygen mask to the oxygen bottle within the support board. The oxygen mask serves as a blood gas exchange means, supplying oxygen to the lungs for exchange with blood gas such as $CO_2$. Optional medicine injectors 50 may be operably connected to the masks or hose to provide for automatic injection of ACLS medications into the airway. The defibrillation module is releasably attached to the support board 28 with quick release latches 51. Tear sheet 46 protects the components of the airway management module during storage and provides ready access for use. An end-tidal $CO_2$ monitor 52 can be included in the mask to provide for biological feedback and monitoring of the success of the CPR. A skin mounted blood oxygen level monitor 53 can also be mounted on the mask for the same purpose (fingertip blood oxygen sensors may also be used, and supplied in the overall assembly to be readily available). The biological data obtained by the sensors is transmitted to the control module via appropriate wiring in the mask and support board.

Figure 11:
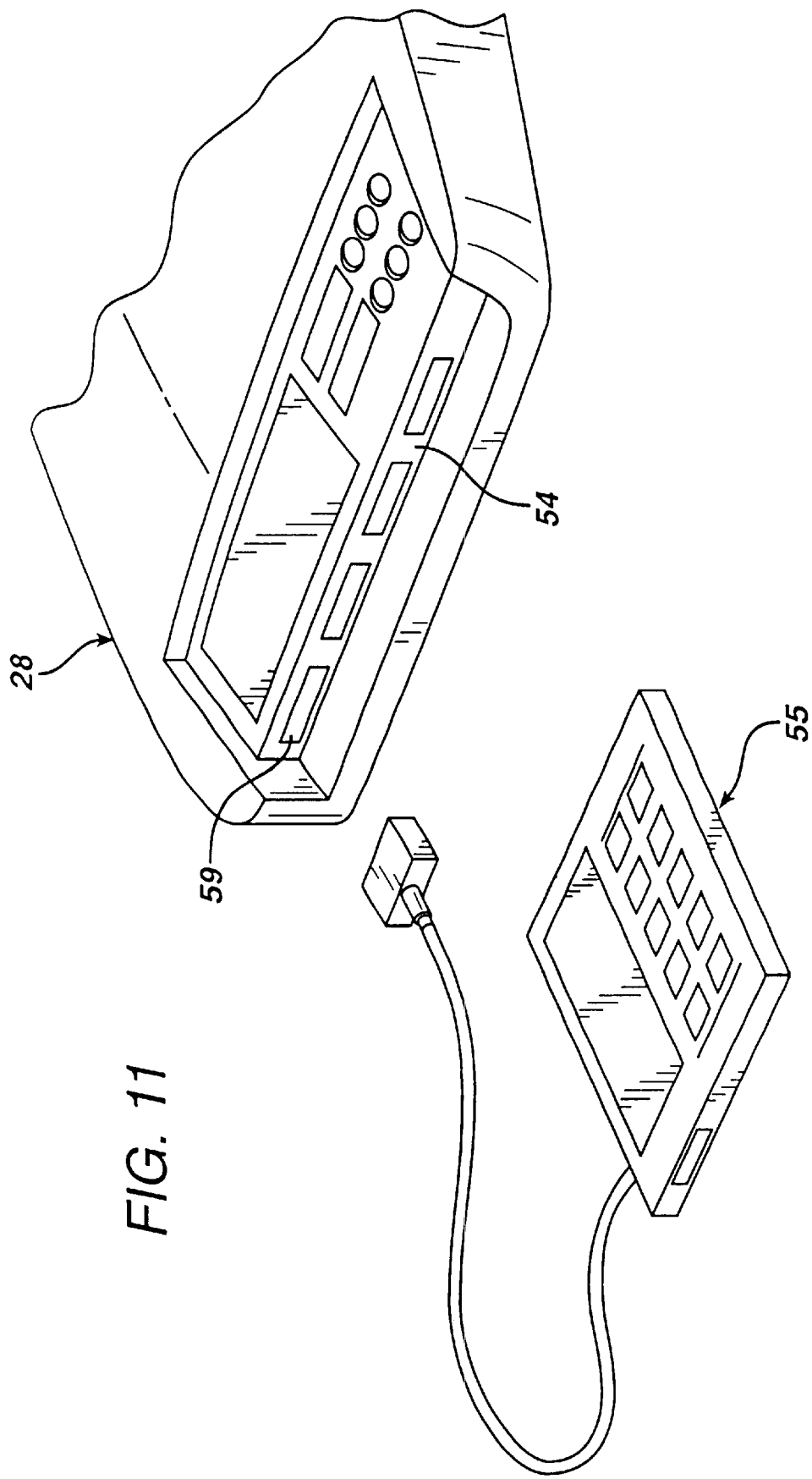
FIG. 11 shows a detail view of the control and communications module of FIG. 7.

FIG. 11 shows a detail view of the control and communications module. The control unit 54 is connected to the compression module, defibrillation module and the airway management module through appropriate wiring through the support board. The control unit is optionally connected to the communications unit 55. The communications unit includes means for communicating the EKG and other measured medical parameters sensed on the board to the screen 56 and via telephone to remote medical personnel. The communications unit can include a telephone handset or speakerphone. Because the device is most likely to be used at a location separate from the storage holder, the communications module preferably includes a wireless communication device, such as wireless telephone, radio telephone or cellular, and any necessary telephone base will be installed in the storage holder.

Figure 12A:
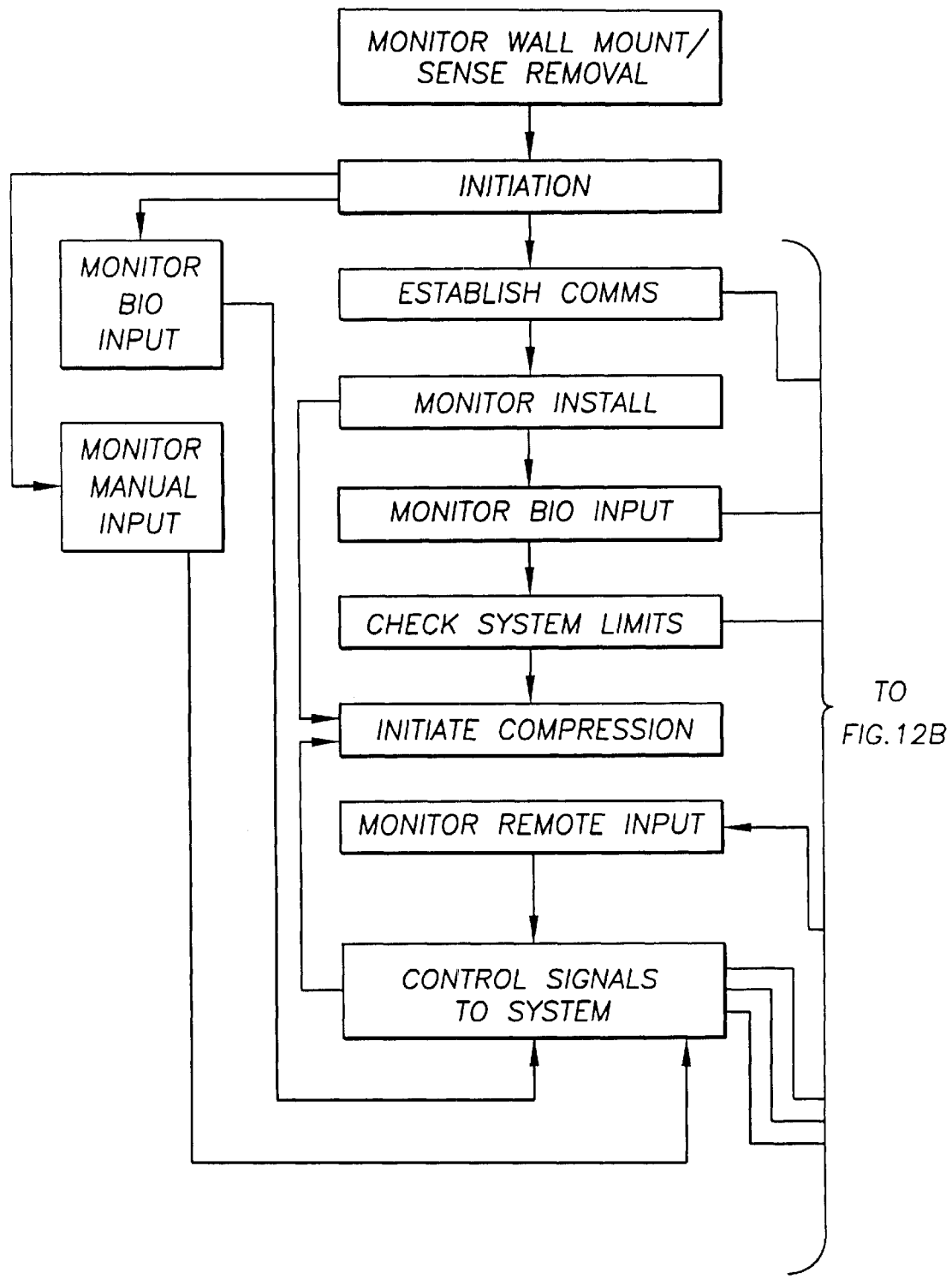
FIG. 12 shows a block diagram of the communications system.

The communications unit and control unit are set up to operate in the following manner, also illustrated in the block diagram of FIG. 12. The device may remain mounted in a charging unit for months between use, and will be removed from the charging unit for use. Upon removal of the device from its storage location, a sensor in the control unit senses the removal (through limit switches, magnetic switches, or motion sensors, current sensors in the charging system, or otherwise) and initiates the system, checking functions, energizing a display unit and accomplishing other typical warm-up functions. As a first step, the system initiates a telephone communication with a medical facility through the communications unit. The communication may use any communication medium, whether it be standard telephone lines, cellular telephone system, paging system or radio transmitter. The system may be set up to initiate communications with central medical facility, such as a local 911 emergency system, a nearby hospital or ambulance service, or a central facility staffed with medical personnel trained specifically on the remote use of the device (all generally referred to as medical personnel). Upon establishing communication, the communications unit informs medical personnel of the location or identification of the device (which may be stored in computer memory in the communications unit, or determined through GPS or other such system), and this information can be used to dispatch an emergency medical team to the location of the device. In a simple embodiment which does not require a computer to control the actions of the alert feature, the removal sensor may comprise a limit switch, while the communications module may comprise a simple telephone unit installed in the storage holder together with a tape recorded message, where the operation of the relay in response to removal of the resuscitation device includes initiation of the telephone call to 911 and playback of an alert message providing alert information such as the location of the board. The communications unit may also be provided with an alert button that may be operated by a bystander regardless of the use of the board to summon an emergency team to the location regardless of the condition of the resuscitation device.

Before the emergency medical team arrives, a bystander will place the board under the victim, buckle the compression belt around the victim and apply defibrillation and/or sensing electrodes (or vice versa)(alternatively, sensing electrodes can be included on the inner surface of the compression belt). The system monitors the installation of the belt through signals provided through latching sensors in the buckle. The system monitors biological input, which can comprise monitoring of EKG signals from the EKG electrode patches of the defibrillation module, monitoring EKG signals belt mounted electrodes, monitoring signals from an end-tidal $CO_2$ monitor from the airway management module, and any other biological signal sensor incorporated into the device. The system can also monitor or respond to manually inputted instruction from the control unit, in order to provide on-site emergency medical personnel with control of the device when they arrive on scene. During operation, the system transmits all available biological information, including EKG signals, blood pressure, end-tidal $CO_2$ and any other monitored biological parameter to the remote medical facility, and it can also transmit information regarding the configuration of the device, including battery life, system operating limit settings (i.e., whether the system is set for automatic operation, permissive operation, or disabled in any function) so that medical personnel can ensure that the appropriate configuration is in effect.

Communication with the medical facility will allow emergency medical personnel to diagnose the condition of the patient and, through signals sent from the medical personnel to the communications unit, permit, initiate or prohibit certain additional therapeutic ACLS actions. For example, upon diagnosing the EKG conditions that indicate the need for defibrillation, the medical personnel can send a signal to the communications unit that acts upon the control unit to permit manual operation of the defibrillation electrodes by the bystander. The system also provides for application of a defibrillation shock via remote signal from the medical personnel. The device can incorporate the expert system such as the Automatic External Defibrillator. The medical personnel can also communicate other actions, and ensure that certain acts are undertaken by the bystander through the communication system. For example, the medical personnel may communicate verbally with the bystander to ascertain the cause of the cardiac arrest, the proper placement of the oxygen mask, appropriate clearing of the airway, and other information. Where the airway management module is provided with medication such as epinephrine, lidocaine, bretylium or other drugs called for in the ACLS guidelines (or newly proposed drugs such as T3), the medical personnel can instruct by-standers to inject appropriate medication through the airway. Where automatic injectors such as those described in Kramer, Interactive External Defibrillation and Drug Injection System, U.S. Pat. No. 5,405,362 (Apr. 11, 1995) are provided, or similar system with non-osseous injectors are provided, the medical personnel can instruct by-standers to inject appropriate medication through these injectors. Where the injectors are provided with means for automatic operation based on measured EKG signals, blood pressure and end-tidal $CO_2$, the medical personnel can send signals to the system to initiate injection by remote control of the medical personnel, permit injection by local control as determined by the expert system, permit injection by by-standers, or prohibit injection by the system or bystanders. For example, the system can be initially set up to forbid any injection. Medical personnel, having diagnosed ventricular fibrillation through the information provided by the communications unit, can send an appropriate signal to permit or initiate injection of epinephrine, and also send a signal to prohibit injection of atropine until called for under the ACLS guidelines. A newly proposed drug T3 can be administered through the airway, into the lungs, as a therapy for cardiac arrest. Controlled injection into the airway can be initiated or prohibited in the same manner. Thus, all actions in the ACLS, including compression, defibrillation, drug injection can be accomplished through the system under the guidance of medical personnel from a remote location, or they may be accomplished through expert systems installed in the control module. Each of these functions in incorporated in a system that automatically initiates communication with medical personnel and informs medical personnel of the location of the device so that emergency medical personnel may be dispatched to the location.

The repeated compression will be initiated upon buckling of the compression belt (automatically) or a switch can be provided for the bystander to initiate compression. The system will continue compression cycles, until de-activated, according the motor control block diagram of FIG. 13. Upon initiation of the system, the control unit will monitor installation of the belt via appropriate sensors in the buckles or through other sensors. When the motor control 57 receives the initiate compression signal from the control unit, the motor is started. The motor is preferably run continuously, rather than stopped and started, to avoid repeated application of startup current and thus conserve battery power. When the motor is up to speed, the clutch is engaged. As a baseline, the clutch is engaged every second for one-half second. This cyclic engagement of the clutch continues repeatedly for five cycles, as recommended by current CPR guidelines, and then is interrupted for a respiration pause, if desired. To avoid excessive drain on the batteries, the motor controller includes a torque sensor (sensing current supply to the motor, for example), and monitors the torque or load on the motor. A threshold is established above which further compression is not desired or useful, and if this occurs during the half second of clutch engagement, then the clutch is disengaged and the cycle continues. The system can monitor the effectiveness of the compression stroke by monitoring the $CO_2$ content of the victim's exhalant. Where $CO_2$ content is low, indicating inadequate circulation, the control system increases the torque limit until the $CO_2$ levels are acceptable (or until the maximum torque of the motor is achieved.) This is another example of the device's use of biological signals to control operation of the system. The cycle time and period, number of cycles between respiration pauses, and the torque limit, can be set according to current guidelines, and can also be varied by the remote medical personnel via the remote control capabilities of the control unit.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A resuscitation and alert system comprising:
 a resuscitation device comprising a chest compression device, the chest compression device having a compression belt and a buckle for securing the compression belt around the chest of a victim;
 a sensor, attached to the buckle, for determining when the buckle has been latched thereby indicating that the resuscitation device is in use, the sensor having an output;
 a computer storage device for storing information corresponding to the location of the resuscitation device;
 a communication device for communicating with an emergency medical system; and
 a computer controller, responsive to the output of the sensor, for initiating the communication device and for relaying the information stored on the computer storage device through the communication device to the emergency medical system.

2. The system of claim 1, further comprising:
 at least one rechargeable battery operatively connected to the resuscitation device, said recharable battery having charging connections for connecting the rechargable battery to an electrical power supply for charging the battery when not in use; and
 a disconnection sensor for sensing the disconnection of the resuscitation device from the charging connection, the disconnection sensor having an output;
 wherein the communication device, responsive to the output from the disconnection sensor, initiates a communication with an emergency medical system that the resuscitation device has been disconnected from the charging connection.

3. The system of claim 1, wherein the communication device comprises a telephone controlled by the computer controller, the computer controlled is programmed to initiate a telephone call to a 911 emergency system and communicate the information corresponding to the location of the resuscitation device to the 911 emergency medical system.

* * * * *